(12) United States Patent
Gassner

(10) Patent No.: US 7,877,171 B2
(45) Date of Patent: Jan. 25, 2011

(54) SWITCHING DEVICE FOR MEDICAL OR SURGICAL EQUIPMENT

(75) Inventor: Stefan Gassner, Immendingen (DE)

(73) Assignee: Aesculap AG, Tuttlingen (DE)

( * ) Notice: Subject to any disclaimer, the term of this patent is extended or adjusted under 35 U.S.C. 154(b) by 520 days.

(21) Appl. No.: 11/986,681

(22) Filed: Nov. 20, 2007

(65) Prior Publication Data

US 2008/0140058 A1  Jun. 12, 2008

(30) Foreign Application Priority Data

Dec. 7, 2006  (DE) ........................ 10 2006 057 682

(51) Int. Cl.
*G05D 1/02* (2006.01)
(52) U.S. Cl. ...................... 700/302; 700/264; 200/86.5; 702/150; 606/1
(58) Field of Classification Search ................. 700/301, 700/264, 302; 600/595; 200/86.5; 606/130; 345/581; 702/150
See application file for complete search history.

(56) References Cited

U.S. PATENT DOCUMENTS

| 5,139,261 | A | * | 8/1992 | Openiano | ..................... 463/36 |
| 5,441,042 | A | | 8/1995 | Putman | |
| 5,837,952 | A | * | 11/1998 | Oshiro et al. | ............. 200/86 R |
| 5,913,727 | A | * | 6/1999 | Ahdoot | ......................... 463/39 |
| 6,110,073 | A | * | 8/2000 | Saur et al. | ....................... 482/8 |
| 6,450,886 | B1 | * | 9/2002 | Oishi et al. | .................... 463/36 |
| 6,572,108 | B1 | * | 6/2003 | Bristow | .................. 273/148 B |
| 6,600,477 | B1 | * | 7/2003 | Howell | ........................ 345/157 |
| 6,659,998 | B2 | * | 12/2003 | DeHoogh et al. | .............. 606/1 |

(Continued)

FOREIGN PATENT DOCUMENTS

EP  0 755 659  1/1997

(Continued)

OTHER PUBLICATIONS

Jaana Leikas, Antti Väätänen, Veli-Pekka Räty, Virtual Space Computer Games with a Floor Sensor Control—Human Centred Approach in the Design Process, Proceedings of the First International Workshop on Haptic Human-Computer Interaction, p. 199-204, Aug. 31-Sep. 01, 2000.*

(Continued)

*Primary Examiner*—Albert DeCady
*Assistant Examiner*—Dave Robertson
(74) *Attorney, Agent, or Firm*—Lipsitz & McAllister, LLC

(57) ABSTRACT

In order to simplify the switching of medical or surgical equipment in an operating theatre, there is proposed a switching device for medical or surgical equipment which is characterized by a planar floor mat having sensors distributed over the surface area thereof, said sensors producing an electrical signal corresponding to the position of a foot of an operator on the floor mat when the foot is located near the respective sensor, and by a data processing system which is connected to the floor mat and is programmed in such a manner that it stores the instantaneous position of the foot on the floor mat as a starting position when activated by an activating signal, selects at least one switching area of the floor mat which has a predetermined location relative to the starting position, and produces a switching signal when the foot is located near a sensor in the switching area.

25 Claims, 1 Drawing Sheet

U.S. PATENT DOCUMENTS

| | | | |
|---|---|---|---|
| 7,060,000 B2 * | 6/2006 | Carlson | 482/1 |
| 7,317,955 B2 * | 1/2008 | McGreevy | 700/83 |
| 7,454,309 B2 * | 11/2008 | Lawrence et al. | 702/160 |
| 7,501,945 B2 * | 3/2009 | Young et al. | 340/539.2 |
| 7,520,836 B2 * | 4/2009 | Couvillion et al. | 482/8 |
| 7,542,040 B2 * | 6/2009 | Templeman | 345/474 |
| 2005/0075545 A1 | 4/2005 | Honda et al. | |
| 2005/0159680 A1 * | 7/2005 | Harbin et al. | 600/587 |
| 2006/0202832 A1 * | 9/2006 | Reznik et al. | 340/572.7 |

FOREIGN PATENT DOCUMENTS

| | | |
|---|---|---|
| WO | 2005/058176 | 6/2005 |

OTHER PUBLICATIONS

W. Couvillion, R. Lopez, J. Ling, "The Pressure Mat: A New Device for Travering Virtual Environments Using Natural Motion," Proc. of the Interservice/Industry Training Simulation and Education Conference, pp. 199-211, 2001.*

Robert Headon, Rupert Curwen, Movement Awareness for Ubiquitous Game Control, Personal and Ubiquitous Computing, v.6 No. 5-6, p. 407-415, Dec. 2002.*

Bouguila, L., Evequoz, F., Courant, M., and Hirsbrunner, B. 2004. Walking-pad: a step-in-place locomotion interface for virtual environments. In Proceedings of the 6th international Conference on Multimodal interfaces (State College, PA, USA, Oct. 13-15, 2004).*

* cited by examiner

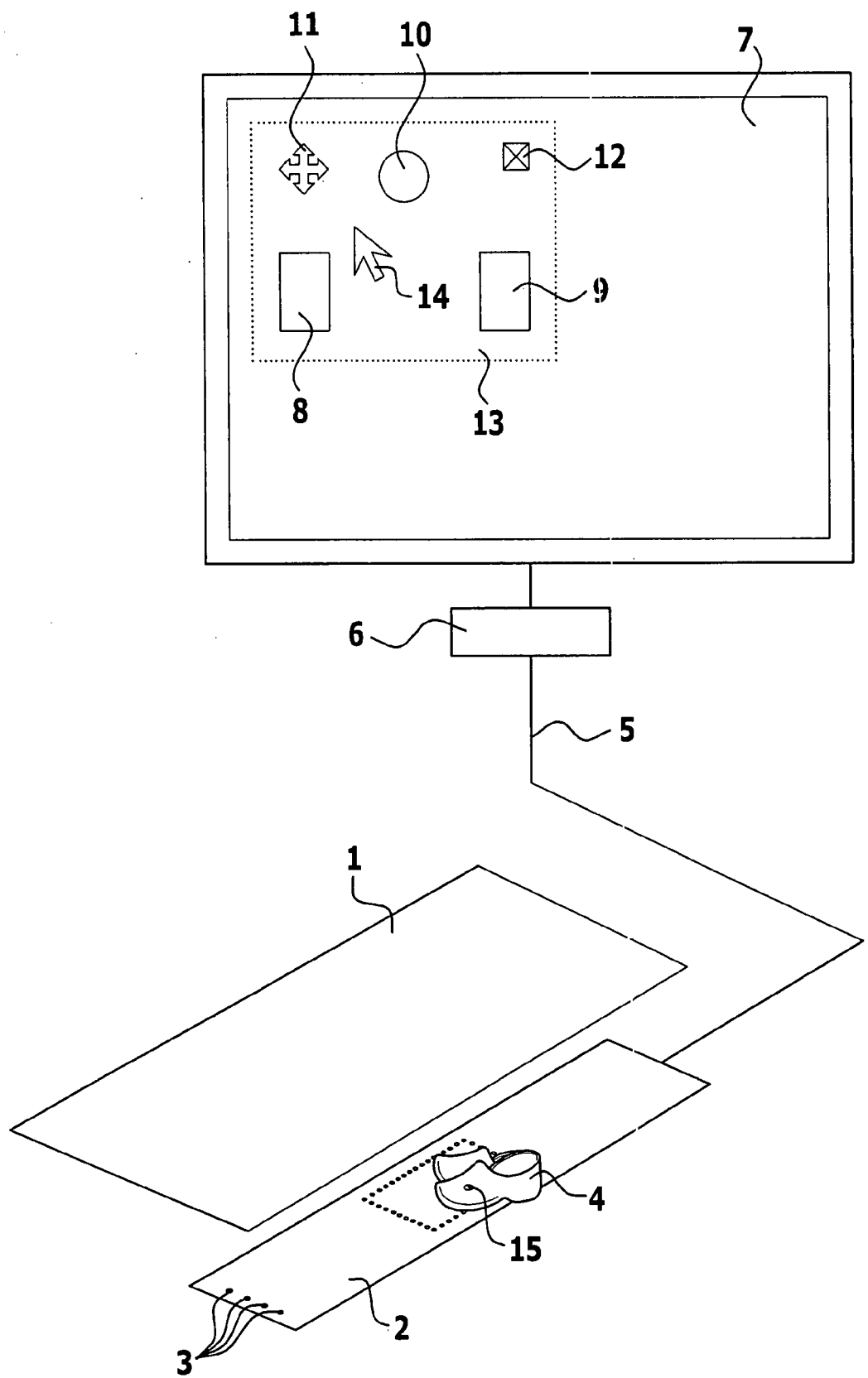

SWITCHING DEVICE FOR MEDICAL OR SURGICAL EQUIPMENT

The invention relates to a switching device for medical or surgical equipment.

For the purposes of controlling software or equipment of this type especially in an operating theatre during surgical operations, use is frequently made of electromechanical foot switches incorporating several switching elements which comprise pedals, manual push-buttons or adjustment knobs for example. Thus, it is known to position foot switches underneath the operating table, these switches being connected to a data processing system by cables or via a wireless transmission line. These foot switches are frequently displaceable so that the operator, an operating physician for example, can drag these foot switches to the particular working position at which he is currently operating. On the other hand, these foot switches can interfere with the work in hand so that the foot switches are frequently pushed away by the operator when they are not needed. It is then necessary to look for these foot switches if they need to be re-utilised, and this means that there is an interruption in the work flow.

In the course of operations of this type, the operator moves around the operating table in the theatre and hence it is difficult to arrange the switching devices in such a way that they can be quickly operated in an uncomplicated manner at the different working positions occupied by the operator.

Consequently, the object here is to produce a switching device for medical or surgical equipment which enables an operator to generate switching signals in the simplest of manners even when there are sometimes frequent changes of position.

In accordance with the invention, this object is achieved by a switching device for medical or surgical equipment which is characterised by a planar floor mat having sensors distributed over the surface area thereof, said sensors producing an electrical signal corresponding to the position of a foot of an operator on the floor mat when the foot is located near the respective sensor, and by a data processing system which is connected to the floor mat and is programmed in such a manner that it stores the instantaneous position of the foot on the floor mat as a starting position when activated by an activating signal, selects at least one switching area of the floor mat which has a predetermined location relative to the starting position, and produces a switching signal when the foot is located near a sensor in the switching area.

A planar floor mat of this type can be laid out in the work area of the operator so that the operator moves around on this floor mat. The respective instantaneous position of a foot of the operator is determined by sensors that are appropriately distributed over the floor mat and this is conveyed to the data processing system. These signals are only used by the data processing system if it has been supplied with an activating signal. If this is the case, then the instantaneous position of the foot is determined and serves for defining a starting position, this starting position being stored in the data processing system. On the basis of this stored starting position, one or preferably several switching areas are defined on the floor mat, said areas having a certain location and being of a certain size relative to this starting position on the floor mat. If the presence of a foot of the operating surgeon in such a switching area is established after such activation by an activating signal, then the electrical signal supplied by the sensor detecting the presence of the foot is interpreted and used by the data processing system as a switching signal.

Thereby, a certain switching function is assigned to a switching area, provision being made for example, for one switching area to switch equipment on and for another switching area to switch this equipment off. Thus, after the activation process, the operator can switch equipment on or off simply by placing his foot in the switching area which is responsible for the switching-on or switching-off process commencing from the starting position defined when the activating signal was produced. Thereby, the movement is always the same since these switching areas are redefined with each activating signal, namely, in such a manner that they are always at the same location and of the same size based upon the instantaneous position of the foot when the activating signal occurs. In consequence, if the switching-on and switching-off regions are accordingly defined, the operator knows for example, that following an activating signal, the switch-on signal will always be 15 centimeters in front of the instantaneous position of his foot and that the switch-off signal is correspondingly 15 centimeters behind this instantaneous position. This applies for every position of the floor mat and is thus independent of the actual position of the operator on the floor mat.

In a simple arrangement of this type in which only one switching-on and one switching-off region are provided for example, the operator does not necessarily need any means for visualizing the geometrical relationships. However, in one preferred embodiment of the invention, provision is made for the switching device to comprise a display device which indicates the switching area or, as the case may be, the switching areas and the respective instantaneous position of the foot of the operator. Hereby, the respective instantaneous position of the foot can be represented in the manner of a cursor on the display means in correspondence with the movement of the foot on the floor mat, whereas the switching areas are represented as being stationary. In consequence, the operating surgeon can follow on the display means the movement of his foot away from the starting position on the floor mat towards a switching area and its arrival there. This is of particular advantage when a larger number of switching areas have been provided and these are distributed around the starting position in a certain manner and the operator must selectively engage them with his foot in order to produce a switching signal.

The display device can be formed in such a manner that it always represents the surroundings of the starting position over the entire display field, but, in accordance with a preferred embodiment, provision can also be made for the switching area or, as the case may be, the switching areas to be represented in a section of the display means and for the positioning of the section on the display means to correspond to the location of the switching areas on the floor mat which is defined by the starting position. Thus, if the operator is located at the left-hand end of the floor mat, then the section too is represented at the left-hand edge of the display means. Consequently, not only is the relative location of his foot with respect to the switching areas indicated to the operator, but so also is his position on the floor mat.

The starting position is maintained fixed after the production of the activating signal. However, in accordance with a preferred embodiment, provision can be made for a displacement switching area which produces a displacement signal if the foot of the operator is displaced on the floor mat commencing from this displacement switching area, whereby the data processing system can then shift the starting position and thus the switching areas in correspondence with the movement of the foot from the displacement switching area to another location on the floor mat and store the new items of positional data. Thus, by moving his foot from the displacement switching area in any arbitrary direction and over any arbitrary distance, it is possible for the operator to shift the starting position on the floor mat in a corresponding manner. In consequence, the switching areas can follow a change of position of the operator on the floor mat.

It is expedient, if provision is made for a switching area that produces a deactivating signal by means of which the production of switching signals is terminated. The operator can thereby interrupt the switching function so that a movement of the operator on the floor mat does not produce switching signals. In the event that the operator should wish to implement a switching function again, then a fresh activating signal must be produced for this purpose.

Provision can also be made for the data processing system to produce a deactivating signal after the expiry of a given time span commencing from the activating signal, said deactivating signal causing the production of switching signals to be terminated. The operator then knows that within this interval of time after the occurrence of the activating signal, a movement of his foot into a switching area will trigger a switching function, but that after the expiry of this time span, the operator is completely free to move his foot without switching signals being produced.

The activating signal can be produced by an acoustic sensor, in particular by a speech recognition system for example.

In another preferred embodiment, provision is made for the activating signal to be produced by the data processing system when a certain sequence of successive signals, a sequence of two signals within a short time period ("doubleclick") for example, are supplied thereto from a single sensor at any desired location on the floor mat. An activating signal is not produced whilst the operator is moving randomly on the floor mat in the course of his work, but should the operator adopt a predetermined sequence of foot positions at some particular location, then this is recognized as an activating signal and leads to the production of a switching signal in the course of a further movement of his foot into a switching area.

After the occurrence of an activating signal, provision can be made for the data processing system to only take into account signals from sensors at which the presence of the foot of the operator has changed after the activating signal. It is thereby ensured that switching signals are only produced by virtue of an intentional movement of the foot of the operator, but not however, by a second foot which remains essentially motionless on the floor mat after the activation process.

The sensors in the floor mat can work according to different physical principles, the essential point being merely that the presence of a foot at a certain location of the floor mat be established. Examples of such sensors are pressure sensors, ultrasonic sensors, capacitive sensors, Hall sensors or analogue resistive sensors.

In particular, provision can also be made for the sensors to respond to the presence of switching elements and for such a switching element to be arranged on a foot of the operator. Such a switching element can, for example, be a permanent magnet which activates magnetic field-sensitive sensors in the floor mat. It is ensured in this way that only one foot of the operator will produce signals of this type in the sensors, but contrariwise, not the other one.

The size of the switching areas on the floor mat and/or their relative location with respect to the starting position can be adjustable so that the operator can freely select these parameters.

In particular, provision can be made for an adjustment switching area on the floor mat which produces a displacement signal if the foot of the operator is displaced away from this adjustment switching area of the floor mat. In this case, the data processing system adjusts the size of the switching areas and/or their relative position with respect to the starting position in correspondence with the movement of the foot from the adjustment switching area to another location on the floor mat.

Such an adjustment switching area can also be used for causing the data processing system to adjust the magnitude of a parameter of a surgical equipment in correspondence with the movement of the foot from the adjustment switching area to another location of the floor mat, for example, the rotational speed of a motor, the strength of a suction unit, the output voltage of a high frequency generator etc.

In accordance with a preferred exemplary embodiment, provision is made for the data processing system to be programmed in such a manner that it shifts the switching area or the switching areas into a new instantaneous position on the floor mat in correspondence with the displacement of the foot if the foot stays at the new instantaneous position for a certain period of time. It is thereby possible for the operating surgeon to change his position and also find the switching areas at their usual position in the new position if he adopts the new position for a certain period of time. In the case of a fast change of position however, the switching areas remain at their old position so that unintentional switching or adjusting signals are not produced as a result of the change.

In accordance with a further preferred embodiment, the data processing system comprises a selecting device for the selective control of various surgical equipment and for the supply of switching and/or adjusting signals thereto. By actuation of the selecting device, one can thus select which equipment is to be supplied by the data processing system with the switching and/or adjusting signals that are produced by the operating surgeon on the floor mat.

In particular, it is advantageous thereby if the data processing system defines different arrangements, sizes and/or numbers of switching areas on the floor mat for various surgical equipments so that, for a certain item of equipment, the operating surgeon will find only one arrangement of switching areas on the floor mat that is applicable to this equipment.

In particular hereby, provision can be made for one or more individual switching areas of the floor mat to be assigned to the selecting device itself so that the operating surgeon can actuate the selecting device by actuating this switching area or these switching areas and can thus switch from one surgical equipment to another. Thus, even in this case, he can exert an influence on the special arrangement of the switching areas for a certain item of equipment.

The following description of preferred embodiments of the invention serves in conjunction with the drawing for a more detailed explanation. The drawing shows a schematic view of the switching device in an operating theatre with a sensor floor mat and a display means.

An operating table 1 upon which a patient is to be operated is located in an operating theatre. The operation is performed by a doctor who moves freely along the edges of the operating table 1 during the operation in order to have access to the patient from all sides.

In the region within which the operating surgeon moves, there is a planar, thin floor mat 2 on the floor of the operating theatre upon which the operating surgeon stands during his work and upon which he moves as necessary.

This floor mat is provided with a large number of sensors 3 which are distributed uniformly over the entire surface area of the floor mat 2. Only a few of these sensors 3 are illustrated in the drawing.

These sensors 3 are formed in such a way that they can establish the position of a foot of the operating surgeon at a certain location on the floor mat 2. In the drawing, shoes 4, the position of which is determined by the sensors 3, are illustrated as being representative of the feet of the operating surgeon.

The sensors can be of differing constructions and work according to different physical principles, for example, they may be pressure sensors, ultrasonic sensors, capacitive or analogue resistive sensors, Hall sensors etc. The sensors can respond directly to the foot or the shoe of the operating surgeon or else, to a switching element which is fastened to a foot of the operating surgeon, for example, a permanent magnet 15.

The density of the sensors 3 on the floor mat 2 is selected in such a way that the position of the foot or that of the shoe 4 can be determined with the desired degree of accuracy, for example, the sensors 3 can be mutually spaced by between 0.5 cm and 5.0 cm.

Preferably, provision is naturally made for the density of the sensors 3 to be relatively high. In particular in this case, it is nevertheless not absolutely necessary for all the sensors to always be active for all the functions. Thus for example, it is possible to activate only every second or every third sensor 3 in the raster for purely switching processes, thus, for example, for a switching-on and switching-off process, but on the other hand, it is expedient to utilise the maximum level of sensitivity and to activate all the sensors 3 if a signal is to be produced which corresponds to the alteration in the position of his foot on the floor mat, thus for example, a signal for adjusting the size of the switching areas or an operating value of surgical equipment.

All of the sensors 3 are connected by a line 5 or else by means of a wireless transmission line to a data processing system 6 with which a display device 7 is also associated, in the form of a screen for example. The display device 7 could also be a pair of spectacles worn by the operating surgeon and into which image data is entered by the data processing system.

The data processing system 6 receives signals from the sensors 3 in the sensitivity regions whereof a foot or a shoe 4 is located. Normally, these signals do not produce an effect in the data processing system 6 so that the operating surgeon can move freely on the floor mat 2 without the signals produced by the sensors 3 and transmitted to the data processing system 6 having any effect.

There is, however, the possibility of activating the data processing system 6 by means of an activating signal. This activating signal can be produced in different ways by the operating surgeon or by an assistant, for example, by means of an acoustic signal, and in particular by virtue of a spoken signal from the operating surgeon. It is also possible for a certain signal sequence from a sensor 3 to be recognized as an activating signal by the data processing system 6. For example, the operating surgeon can move his foot in a certain rapidly repeated sequence at a certain location on the floor mat so that the sensor 3 arranged at this particular location will produce a corresponding sequence of signals. In particular thereby, this may be in the form of a so-called double-click, i.e. two rapidly successive signals occurring within a short period of time. This can be effected from any location of the floor mat 2 since sensors 3 which produce signals of this type that are indicative of the presence of his foot are arranged at every point of the floor mat 2.

If the data processing system 6 is activated by an activating signal in this manner, it determines at which location on the floor mat 2 i.e. near which sensor 3 on the floor mat 2 whereat the foot is located at the moment when the activating signal occurs. This position of the foot or shoe 4 is stored by the data processing system 6 as the starting position and the data processing system 6 thereupon defines one or more switching areas 8, 9, 10, 11, 12 on the floor mat 2 which each have a certain surface area and the location of which relative to the starting position is predetermined. In the exemplary embodiment illustrated here, five switching areas 8 to 12 of this type are defined and these are grouped around the starting position in a predetermined manner.

Sensors 3 are arranged in each switching area, namely, at least one, but preferably a larger number of sensors 3. If the sensors in a switching area are actuated by the presence of a foot in this switching area, they send a corresponding signal to the data processing system and this recognizes these signals as signals which are associated with a certain switching area and consequently triggers off a specific switching function. This may, for example, be a switching-on signal or a switching-off signal for equipment attached to the data processing system.

The operating surgeon can thereby specify a starting position at any position of the floor mat 2 and know that, commencing from this starting position, the switching area for a certain function is always arranged in the same direction and at the same distance and will be of the same size. Based upon this starting position, it is then easily possible for him to contact the desired switching area and thereby produce a switching signal by the presence of his foot alone.

This can even be effected in the simplest case without the aid of a display means, however, it is naturally advantageous if the location of the switching areas 8 to 12 is represented on the display device 7. Moreover, it is advantageous thereby if the instantaneous location of his foot on the floor mat 2, which is ascertainable at any time by the data processing system 6 by virtue of the signals from the sensors 3, is additionally represented on the display device 7 e.g. in the form of a cursor 14. In consequence, the operating surgeon can immediately see on the display means how his foot is positioned relative to the switching areas and can follow the movement of his foot towards a certain switching area.

The display means could be selected in such a manner that the area surrounding the starting position is always represented in the same way over the entire surface of the display device 7 so that the switching areas would then always be located in the same position and only the cursor 14 indicating the position of his foot would move.

Another possibility is chosen in the illustration depicted in the drawing. Namely, the area surrounding the starting position is represented in a section 13, and this section 13, which is smaller than the entire display area of the display device 7, is placed on the display device 7 in correspondence with the location of the starting position on the floor mat 2. Thus, if the starting position is located close to the left-hand edge of the floor mat, then, in correspondence therewith, the section 13 is also positioned at the left-hand edge of the display device 7 etc., so that the operating surgeon can additionally detect his own position on the floor mat 2 by the location of the section 13.

Switching areas 8, 9, 10 for certain switching functions are represented in the illustrated exemplary embodiment, for example, for the purposes of switching-on or switching-off equipment or for changing-over from one mode of operation to another.

In addition, a switching area 11 is provided which is in the form of a displacement switching area. If, after the occurrence of an activating signal, it is determined that the foot of the operating surgeon is in this switching area 11 and if his foot should subsequently move away from the original position to another location on the floor mat 2, then the path pursued by his foot is determined and used by the data processing system 6 in order to make adjustments to certain values in correspondence with the size and/or the direction of the displacement. These values may, for example, be the positioning data for the starting position which was stored after the occurrence of the activating signal. It is thus possible for the operating surgeon to change this starting position whereby the starting position is then shifted synchronously and in the same manner as the movement of his foot on the floor mat and is stored afresh in the new position selected by the operating surgeon. It is thus possible for the operating surgeon to match the location of the switching areas to his instantaneous position if the displacement path is relatively small.

In the case of a displacement signal of this type, other values could also be adjusted, for example, the size of the switching areas or the spacing of the switching areas from the starting position. Consequently, the operating surgeon himself can adjust these sizes individually at any time after the activation process merely by moving his foot onto an appropriate switching area and then moving his foot from this switching area to a new position on the floor mat.

The switching area 12 is in the form of a deactivation region, i.e. positioning of his foot in the switching area 12 leads to the data processing system 6 no longer processing signals that are supplied by the sensors 3 as switching signals. In consequence, the operating surgeon can freely move about again on the floor mat after actuating the deactivation switching area 12 without switching signals thereby being produced.

Provision could also be made for the data processing system 6 to undertake this deactivation process automatically, namely, following the elapse of a certain period of time after the last activating signal for example. In consequence, after the production of an activating signal, the operating surgeon only has at his disposal a certain time window within which the movement of his foot can lead to switching signals.

The signal generating process described above can take place at any position on the floor mat so that the operating surgeon can effect the activation process at any position on the floor mat, produce switching signals at this location and then, after a deactivation process, move freely on the floor mat without incurring unwanted switching signals. A further great advantage of this arrangement is that the floor mat can be manufactured with smooth exterior surfaces and is therefore cleaning-friendly.

The invention claimed is:

1. A switching device for medical or surgical equipment, comprising:
    a planar floor mat having sensors distributed over a surface area thereof, said sensors producing an electrical signal corresponding to a position of a foot of an operator on the floor mat when the foot is located near one or more of the sensors, and
    a data processing system connected to the floor mat and programmed to:
    store the instantaneous position of the foot on the floor mat as a starting position when activated by an activating signal,
    select at least one corresponding switching area of the floor mat,
    and produce a switching signal only when the foot is located near one or more of the sensors in the at least one corresponding switching area;
    wherein the instantaneous starting position may be at any position on the floor mat near one or more of the sensors, and
    wherein the at least one corresponding switching area of the floor mat is a location on the floor mat at a predetermined distance and direction relative to the starting position.

2. A switching device in accordance with claim 1, further comprising a display device which indicates the at least one switching area and the corresponding instantaneous position of the foot of the operator.

3. A switching device in accordance with claim 2, wherein the at least one switching area is represented in a section of the display device and a location of the section on the display device corresponds to a location of the at least one switching area on the floor mat that is defined by the starting position.

4. A switching device in accordance with claim 1, wherein there is provided a displacement switching area which produces a displacement signal if the foot of the operator is displaced on the floor mat commencing from this displacement switching area, and the data processing system shifts the starting position and thus the at least one switching area to a new starting position and a new switching position in correspondence with movement of the foot from the displacement switching area to another location on the floor mat and stores positional data relating to the new starting position and the new switching position.

5. A switching device in accordance with claim 1, wherein there is provided a switching area which produces a deactivating signal by means of which the production of switching signals is terminated.

6. A switching device in accordance with claim 1, wherein after expiry of a given time interval commencing from the activating signal, the data processing system produces a deactivating signal by means of which the production of switching signals is terminated.

7. A switching device in accordance with claim 1, wherein the activating signal is produced by an acoustic sensor.

8. A switching device in accordance with claim 1, wherein the activating signal is produced by the data processing system if a certain sequence of successive signals is supplied thereto from a single sensor at an arbitrary location on the floor mat.

9. A switching device in accordance with claim 8, wherein the sequence consists of two signals within a short time period.

10. A switching device in accordance with claim 1, wherein following the activating signal, the data processing system only takes into account signals from sensors at which a presence of the foot of the operator has changed after the activating signal.

11. A switching device in accordance with claim 1, wherein the sensors are pressure sensors in the floor mat.

12. A switching device in accordance with claim 1, wherein the sensors are ultrasonic sensors in the floor mat.

13. A switching device in accordance with claim 1, wherein the sensors are capacitive sensors in the floor mat.

14. A switching device in accordance with claim 1, wherein the sensors are Hall sensors in the floor mat.

15. A switching device in accordance with claim 1, wherein the sensors are analogue resistive sensors in the floor mat.

16. A switching device in accordance with claim 1, wherein the sensors respond to a presence of a switching element arranged on a foot of the operator.

17. A switching device in accordance with claim 1, wherein at least one of a size of the at least one switching area on the floor mat and a relative location of the at least one switching area with respect to the starting position are adjustable.

18. A switching device in accordance with claim 17, wherein there is provided an adjustment switching area which produces a displacement signal if the foot of the operator is displaced from the adjustment switching area of the floor mat, and the data processing system adjusts at least one of the size of the at least one switching area and the relative location of the at least one switching area with respect to the starting position in correspondence with movement of the foot from the adjustment switching area to another location on the floor mat.

19. A switching device in accordance with claim 1, wherein there is provided an adjustment switching area which produces a displacement signal if the foot of the operator is displaced from the adjustment switching area of the floor mat, and the data processing system adjusts a magnitude of a parameter of a surgical equipment in correspondence with movement of the foot from the adjustment switching area to another location on the floor mat.

20. A switching device in accordance with claim 1, wherein the data processing system is programmed in such a manner that it shifts the at least one switching area into a new instantaneous position on the floor mat in correspondence with a displacement of the foot if the foot stays at the new instantaneous position for a certain period of time.

21. A switching device in accordance with claim 1, wherein the data processing system comprises a selecting device for selective control of various surgical equipment and a supply of switching and/or adjusting signals thereto.

22. A switching device in accordance with claim 21, wherein the data processing system defines different arrangements, sizes and/or numbers of switching areas on the floor mat for various surgical equipment.

23. A switching device in accordance with claim 21, wherein one or more individual switching areas of the floor mat are assigned to the selecting device.

24. A switching device in accordance with claim 4, wherein following the activating signal, the data processing system only takes into account signals from sensors at which a presence of the foot of the operator has changed after the activating signal.

25. A switching device in accordance with claim 4, wherein there is provided an adjustment switching area which produces a displacement signal if the foot of the operator is displaced from the adjustment switching area of the floor mat, and the data processing system adjusts a magnitude of a parameter of a surgical equipment in correspondence with movement of the foot from the adjustment switching area to another location on the floor mat.

* * * * *